(12) United States Patent
Cerundolo

(10) Patent No.: US 7,963,983 B2
(45) Date of Patent: Jun. 21, 2011

(54) FIXATION DEVICE FOR SURGICAL REPAIR

(75) Inventor: Daniel Cerundolo, Hingham, MA (US)

(73) Assignee: Arthroscopic Innovations LLC, Weymouth, MA (US)

( * ) Notice: Subject to any disclaimer, the term of this patent is extended or adjusted under 35 U.S.C. 154(b) by 659 days.

(21) Appl. No.: 11/582,213

(22) Filed: Oct. 17, 2006

(65) Prior Publication Data

US 2008/0177336 A1    Jul. 24, 2008

(51) Int. Cl.
  A61B 17/04    (2006.01)
  A61B 17/86    (2006.01)
  A61F 2/08    (2006.01)
(52) U.S. Cl. ............................ 606/321; 606/232
(58) Field of Classification Search .............. 606/321, 606/232, 302, 306, 310, 319, 322, 323, 328
  See application file for complete search history.

(56) References Cited

U.S. PATENT DOCUMENTS

| | | | |
|---|---|---|---|
| 4,744,793 A | 5/1988 | Parr et al. | |
| 4,828,562 A | 5/1989 | Kenna | |
| 5,129,902 A | 7/1992 | Goble | |
| 5,234,435 A | 8/1993 | Seagrave | |
| 5,258,016 A * | 11/1993 | DiPoto et al. | 606/232 |
| 5,383,905 A * | 1/1995 | Golds et al. | 606/232 |
| 5,464,427 A * | 11/1995 | Curtis et al. | 606/232 |
| 5,707,395 A | 1/1998 | Li | |
| 5,725,529 A | 3/1998 | Nicholson et al. | |
| 5,871,504 A | 2/1999 | Eaton et al. | |
| 5,899,938 A | 5/1999 | Sklar et al. | |
| 5,916,216 A | 6/1999 | DeSatnick et al. | |
| 5,918,604 A * | 7/1999 | Whelan | 128/898 |
| 5,931,869 A | 8/1999 | Boucher | |
| 5,961,520 A | 10/1999 | Beck | |
| 5,964,764 A | 10/1999 | West, Jr. et al. | |
| 6,086,591 A | 7/2000 | Bojarski | |
| 6,096,060 A | 8/2000 | Fitts et al. | |
| 6,099,530 A | 8/2000 | Simonian et al. | |

(Continued)

FOREIGN PATENT DOCUMENTS

EP    0464479 A    1/1992

(Continued)

OTHER PUBLICATIONS

International Search Report PCT/US2007/022041, dated Mar. 31, 2008.

(Continued)

*Primary Examiner* — Thomas C Barrett
*Assistant Examiner* — David W Bates
(74) *Attorney, Agent, or Firm* — Wolf, Greenfield & Sacks, P.C.

(57) ABSTRACT

A method and apparatus for performing a surgical repair may involve fixation of a repair material, such as a ligament or tendon in knee ligament repair procedure, to an internal cortical contact area in a bone. The cortical bone contact area may be located immediately adjacent an opening in the bone's surface through which the repair material extends. The repair material may be engaged with the contact area by way of a fixation device, such as a device that is attached to the repair material and functions as a stop member. An illustrative fixation device may include an annular portion with an aperture through with the repair material passes. The repair material may be attached to a securing portion that extends from the annular portion.

41 Claims, 5 Drawing Sheets

U.S. PATENT DOCUMENTS

| | | | |
|---|---|---|---|
| 6,099,568 A | 8/2000 | Simonian | |
| 6,113,604 A | 9/2000 | Whittaker et al. | |
| 6,117,139 A | 9/2000 | Shino | |
| 6,123,711 A | 9/2000 | Winters | |
| 6,152,928 A | 11/2000 | Wenstrom, Jr. | |
| 6,162,234 A | 12/2000 | Freedland | |
| 6,214,007 B1 * | 4/2001 | Anderson | 606/304 |
| 6,221,107 B1 | 4/2001 | Steiner et al. | |
| 6,231,606 B1 | 5/2001 | Graf et al. | |
| 6,235,057 B1 | 5/2001 | Roger et al. | |
| 6,235,058 B1 | 5/2001 | Huene | |
| 6,245,073 B1 | 6/2001 | Conteduca | |
| 6,264,694 B1 | 7/2001 | Weiler | |
| 6,306,138 B1 | 10/2001 | Clark et al. | |
| 6,325,804 B1 | 12/2001 | Wenstrom et al. | |
| 6,336,940 B1 | 1/2002 | Graf et al. | |
| 6,355,066 B1 | 3/2002 | Kim | |
| 6,364,886 B1 | 4/2002 | Sklar | |
| 6,371,124 B1 | 4/2002 | Whelan | |
| 6,379,361 B1 | 4/2002 | Beck, Jr. et al. | |
| 6,379,384 B1 | 4/2002 | McKernan et al. | |
| 6,387,129 B2 | 5/2002 | Rieser et al. | |
| 6,419,700 B2 | 7/2002 | Huene | |
| 6,436,099 B1 * | 8/2002 | Drewry et al. | 606/300 |
| 6,440,134 B1 | 8/2002 | Zaccherotti et al. | |
| 6,461,373 B2 | 10/2002 | Wyman et al. | |
| 6,464,706 B1 | 10/2002 | Winters | |
| 6,482,210 B1 | 11/2002 | Skiba et al. | |
| 6,482,232 B1 | 11/2002 | Boucher et al. | |
| 6,499,486 B1 | 12/2002 | Chervitz et al. | |
| 6,517,546 B2 | 2/2003 | Whittaker et al. | |
| 6,517,579 B1 | 2/2003 | Paulos et al. | |
| 6,533,816 B2 | 3/2003 | Sklar | |
| 6,544,281 B2 | 4/2003 | Elattrache et al. | |
| 6,554,862 B2 | 4/2003 | Hays et al. | |
| 6,562,043 B1 | 5/2003 | Chan | |
| 6,562,071 B2 | 5/2003 | Jarvinen | |
| 6,579,295 B1 | 6/2003 | Supinski | |
| 6,599,289 B1 | 7/2003 | Bojarski et al. | |
| 6,616,694 B1 | 9/2003 | Hart | |
| 6,620,195 B2 | 9/2003 | Goble et al. | |
| 6,623,524 B2 | 9/2003 | Schmieding | |
| 6,632,245 B2 | 10/2003 | Kim | |
| 6,652,560 B1 | 11/2003 | Gerke et al. | |
| 6,685,709 B2 | 2/2004 | Sklar | |
| 6,712,849 B2 | 3/2004 | Ke et al. | |
| 6,716,217 B2 | 4/2004 | McKernan et al. | |
| 6,733,529 B2 | 5/2004 | Whelan | |
| 6,736,847 B2 | 5/2004 | Reay-Young et al. | |
| 6,752,830 B1 | 6/2004 | Goble et al. | |
| 6,755,840 B2 | 6/2004 | Boucher et al. | |
| 6,780,188 B2 | 8/2004 | Clark et al. | |
| 6,802,862 B1 | 10/2004 | Roger et al. | |
| 6,808,528 B2 | 10/2004 | Justin | |
| 6,833,055 B2 | 12/2004 | Hansen et al. | |
| 6,875,214 B2 | 4/2005 | Supinski | |
| 6,878,166 B2 | 4/2005 | Clark et al. | |
| 6,886,569 B2 | 5/2005 | Chervitz et al. | |
| 6,887,271 B2 | 5/2005 | Justin et al. | |
| 6,902,573 B2 | 6/2005 | Strobel | |
| 6,932,841 B2 | 8/2005 | Sklar et al. | |
| 6,939,379 B2 | 9/2005 | Sklar | |
| 6,958,067 B2 | 10/2005 | Whittaker et al. | |
| 2001/0047206 A1 | 11/2001 | Sklar | |
| 2002/0133165 A1 | 9/2002 | Whittaker et al. | |
| 2002/0156476 A1 | 10/2002 | Wilford | |
| 2002/0156484 A1 | 10/2002 | McKernan et al. | |
| 2002/0165546 A1 | 11/2002 | Goble et al. | |
| 2002/0165547 A1 | 11/2002 | Dovesi et al. | |
| 2002/0173795 A1 | 11/2002 | Sklar | |
| 2002/0173849 A1 | 11/2002 | McKernan | |
| 2002/0188298 A1 | 12/2002 | Chan | |
| 2003/0009217 A1 | 1/2003 | McKernan | |
| 2003/0009218 A1 | 1/2003 | Boucher et al. | |
| 2003/0009219 A1 | 1/2003 | Seyr et al. | |
| 2003/0040795 A1 | 2/2003 | Elson et al. | |
| 2003/0065390 A1 | 4/2003 | Justin et al. | |
| 2003/0065391 A1 | 4/2003 | Re et al. | |
| 2003/0100903 A1 | 5/2003 | Cooper | |
| 2003/0120278 A1 | 6/2003 | Morgan | |
| 2003/0120343 A1 | 6/2003 | Whelan | |
| 2003/0130666 A1 | 7/2003 | Whittaker et al. | |
| 2003/0135274 A1 | 7/2003 | Hays et al. | |
| 2003/0191530 A1 | 10/2003 | Sklar | |
| 2003/0216780 A1 | 11/2003 | Fitts et al. | |
| 2004/0006349 A1 | 1/2004 | Goble et al. | |
| 2004/0015237 A1 | 1/2004 | Whittaker et al. | |
| 2004/0049195 A1 | 3/2004 | Singhatat et al. | |
| 2004/0059415 A1 | 3/2004 | Schmieding | |
| 2004/0068262 A1 | 4/2004 | Lemos et al. | |
| 2004/0073306 A1 | 4/2004 | Eichhorn | |
| 2004/0087953 A1 | 5/2004 | Singhatat et al. | |
| 2004/0092936 A1 | 5/2004 | Miller et al. | |
| 2004/0097943 A1 | 5/2004 | Hart | |
| 2004/0097945 A1 | 5/2004 | Wolf | |
| 2004/0097977 A1 | 5/2004 | Goble | |
| 2004/0153076 A1 | 8/2004 | Singhatat et al. | |
| 2004/0153153 A1 | 8/2004 | Elson et al. | |
| 2004/0220576 A1 | 11/2004 | Sklar | |
| 2004/0225358 A1 | 11/2004 | Goble et al. | |
| 2004/0230302 A1 | 11/2004 | May et al. | |
| 2004/0243132 A1 | 12/2004 | Whittaker | |
| 2004/0267318 A1 | 12/2004 | Boucher et al. | |
| 2004/0267361 A1 | 12/2004 | Donnelly et al. | |
| 2005/0010289 A1 | 1/2005 | McKernan et al. | |
| 2005/0033301 A1 | 2/2005 | Lombardo et al. | |
| 2005/0038426 A1 | 2/2005 | Chan | |
| 2005/0096743 A1 | 5/2005 | Schmieding et al. | |
| 2005/0137704 A1 | 6/2005 | Steenlage | |
| 2005/0149187 A1 | 7/2005 | Clark et al. | |
| 2005/0159748 A1 | 7/2005 | Clark | |
| 2005/0159812 A1 | 7/2005 | Dinger, III et al. | |
| 2005/0171603 A1 | 8/2005 | Justin | |
| 2005/0197662 A1 | 9/2005 | Clark et al. | |
| 2005/0216014 A1 | 9/2005 | May et al. | |
| 2005/0234469 A1 | 10/2005 | Whittaker et al. | |
| 2006/0015107 A1 | 1/2006 | Sklar | |

FOREIGN PATENT DOCUMENTS

| | | |
|---|---|---|
| WO | WO0064363 A | 11/2000 |
| WO | WO02/32345 A2 | 4/2002 |
| WO | WO0232345 A | 4/2002 |
| WO | WO03000783 A | 2/2003 |

OTHER PUBLICATIONS

U.S. Appl. No. 11/582,185, filed Oct. 17, 2006, Daniel Cerundolo.

Scandius Biomedical, Inc., Stratis™ ST Femoral Fixation System, Surgical Technique Guide, Preparing the Graft Block/Graft Construct, pp. 1-10, 2005.

Stuart Fromm, M.D., Smith & Nephew, Inc., Endobutton CL BTB, Fixation System, pp. 1-10, 2004.

* cited by examiner

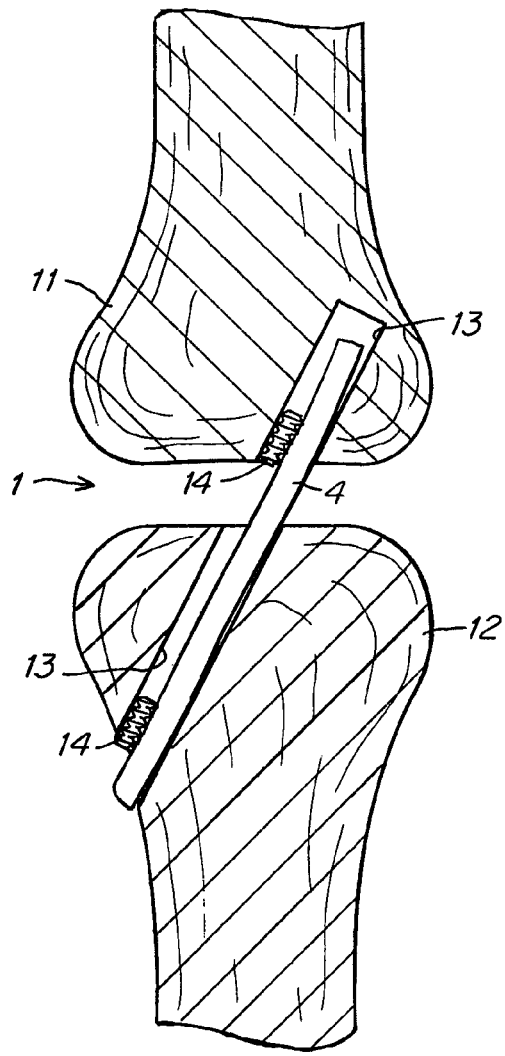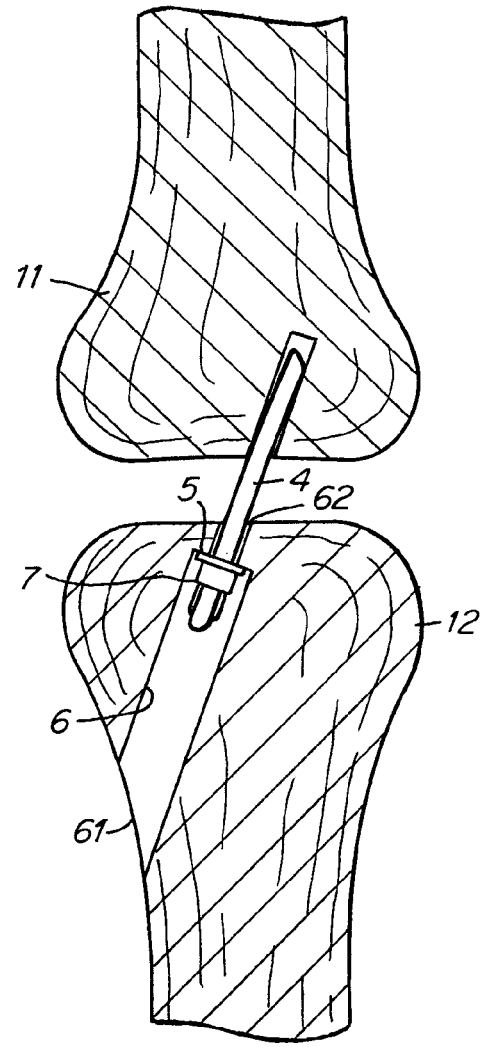
Fig. 3
PRIOR ART
Fig. 4

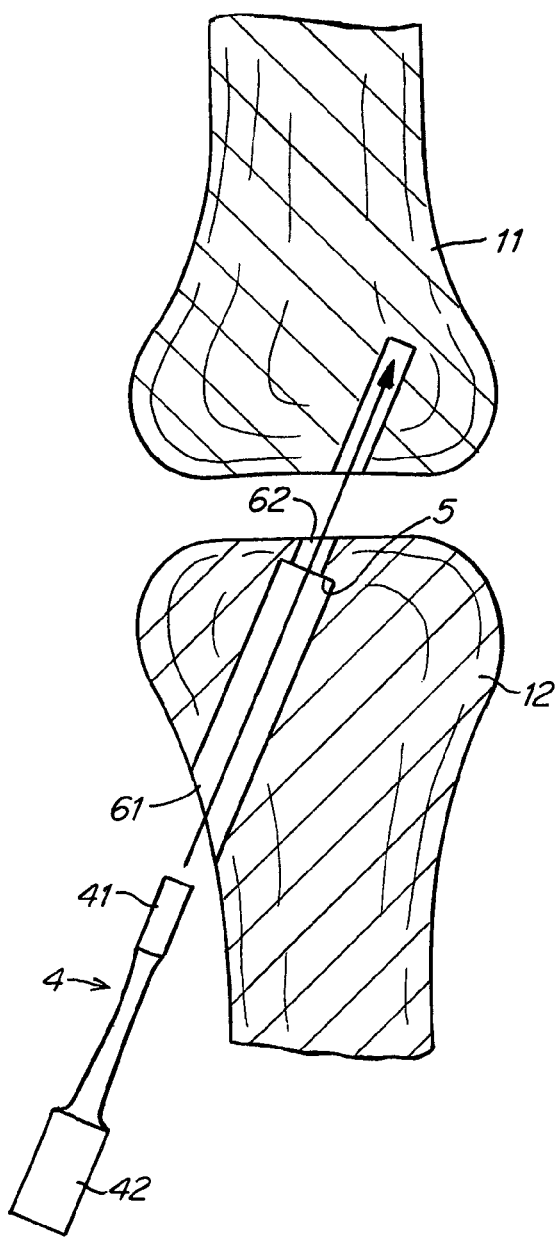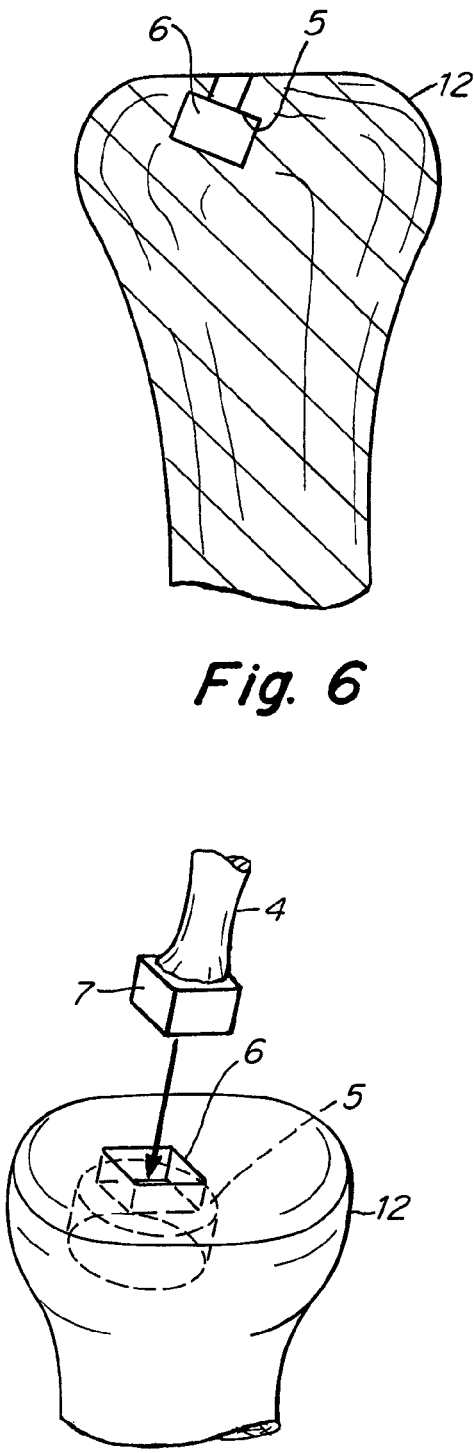
Fig. 6
Fig. 5
Fig. 7

FIXATION DEVICE FOR SURGICAL REPAIR

BACKGROUND OF INVENTION

1. Field of Invention

This invention relates to methods and apparatus for surgical repair.

2. Discussion of Related Art

Fixation devices are often used for surgical repair, such as when attempting to secure one body portion relative to another or relative to a surgical implant or other device. For example, tendon or ligament damage frequently requires surgery for repair, e.g., to reattach a torn or separated tendon or ligament to the bone to which the tendon/ligament would normally be attached. Knee ligament injuries typically involve damage to one or more ligaments such that a ligament, or at least a portion thereof, requires reattachment to the tibia and/or femur. FIG. 1 shows a schematic diagram of a knee 1 and a portion of a ligament 2 (e.g., an anterior cruciate ligament, or ACL, that is normally attached between the femur 11 and the tibia 12. In one type of damage to the ligament 2, the ligament 2 may detach or be partially torn from the femur 11 and/or tibia 12, such as that shown schematically in FIG. 2. Such damage may be repaired by replacing the ligament 2 with a graft or other repair material, as is known in the art. One repair technique for replacing the ligament 2 involves drilling holes 13 in both the femur 11 and tibia 12, and fixing the graft 14 in both holes, e.g., using interference screws 14 as shown in FIG. 3.

SUMMARY OF INVENTION

In one aspect of the invention, a ligament repair technique is provided that does not necessarily require the use of an interference screw to secure the ligament to a bone. In one embodiment, a portion of the bone itself may support the ligament without the need for an interference screw or other fixation device. In another embodiment, a fixation device, if provided, may be positioned in contact with an interior bone surface, e.g., a cortical bone surface, to secure the ligament in place In one aspect of the invention, a surgical repair method includes forming an opening in a first bone, with the opening having a first size at an outer surface of the first bone. For example, the first bone may be a tibia, and the opening may be formed in a portion of the tibia near where a knee ligament, such as an ACL, is normally attached. A contact area is then formed inside the first bone, with the contact area being formed, at least in part, by cortical bone located near the opening inside the first bone's outer surface and having a size that is larger than the first size. For example, the contact area may be formed by an annular surface of the cortical bone inside the tibia and surrounding the opening. A first end of a joint repair material may be secured to the contact area in the opening, and the joint repair material may be positioned to extend from within the first bone at the contact area out through the opening. For example, a graft ligament may be secured to the contact area and extend out of the opening toward the femur. A second end of the joint repair material opposite the first end may be secured to a body member distinct from the first bone, e.g., the graft ligament may be secured to a femur, thereby connecting the tibia and femur. Although in this example the joint repair material is a graft ligament, the joint repair material may be any suitable naturally-occurring material (such as an autograft or allograft material), a synthetic material, or any suitable combination of natural and synthetic materials.

In another aspect of the invention, a surgical repair method includes forming a passageway through a bone with respect to which a joint repair material is to be fixated such that the passageway extends from a first opening to a second opening. A contact area may be formed inside the bone, so that the contact area is defined, at least in part, by cortical bone located inside the bone's outer surface near the second opening. A first side of the joint repair material may be secured to a fixation device, and the fixation device may be positioned within the bone so that the fixation device is seated at the contact area and the joint repair material extends out of the second opening. In one illustrative embodiment, the passageway may be formed through a tibia so that the second opening and contact area are located near the knee joint. The joint repair material, e.g., a graft ligament, may be secured to a fixation device and fed into the passageway such that the fixation device engages the contact area (securing the graft relative to the tibia) and the graft extends from the second opening. The graft may be secured to a femur using any suitable technique to complete the ligament repair. Thus, the fixation device may engage the contact area so that the fixation device resists tension placed on the joint repair material to pull the joint repair material from the passageway and out of the second opening.

The passageway may be formed so that the second opening has a smaller size than the first opening. In one embodiment, the passageway may be formed by forming a hole through the bone, with the hole having a size approximately equal to the size of the second opening. A counterbore may be formed in the hole to form the first opening and the contact area. Cancellous bone in the passageway may be displaced (e.g., compacted, removed, etc.) to expose an area of cortical bone in the passageway.

In another aspect of the invention, a surgical fixation device includes a base portion with an aperture constructed and arranged to receive a joint repair material, such as a graft ligament. The base portion has a contact surface and is constructed and arranged to contact a bone at the contact surface and secure the joint repair material relative to the bone. The fixation device also may include a securing portion constructed and arranged to secure the joint repair material relative to the base portion. The securing portion is arranged to engage with the base portion on a side of the base portion opposite the contact surface. The base portion and the securing portion may be arranged to be deployed entirely within a bone opening, e.g., such that no portion of the fixation device is located outside of the bone, and to resist tension applied on the joint repair material secured to the securing portion in a direction from the securing portion toward the contact surface. In addition, the securing portion may be arranged to position the joint repair material in contact with bone in the bone opening, e.g., to encourage attachment of the graft to the bone by healing processes.

In another aspect of the invention, a surgical fixation device includes an annular portion having a bone contact surface on a first side and an opening adapted to receive a ligament repair material. A securing portion may be arranged to engage with a second side of the annular portion opposite the first side. The securing portion may have an elongated member extending in a direction away from the contact surface when engaged with the annular portion, and may be adapted to secure a ligament repair material passing through the opening to the annular portion. The annular portion and the securing portion may be arranged to be deployed entirely within a bone opening and to resist tension applied on the ligament repair material secured to the securing portion in a direction from the securing portion toward the contact surface.

In one embodiment, at least a portion of the securing portion extends across the opening in the annular portion. Also, the elongated member of the securing portion may include opposed grooves to receive the joint repair material, and may have one or more openings adapted to receive suture to secure the ligament repair material to the securing portion. The elongated member of the securing portion may have a Y-shape with two legs attached to the annular portion (e.g., on opposite sides of the opening) and one leg extending away from the annular portion. The securing portion may also taper so as to be thinner in a region near the opening in the flange and so as to be thicker in a region positioned away from the opening. The base and securing portions may be made of a non-absorbable, biocompatible material, such as titanium, and/or an absorbable material, such as polylactic acid (PLA), and/or other materials or combinations of materials.

Other aspects of the invention are provided that are not necessarily restricted to use in knee ligament repair. Instead, aspects of the invention may be used in other surgical repair techniques in which a ligament, tendon, prosthetic or other material is secured relative to bone.

BRIEF DESCRIPTION OF DRAWINGS

Various aspects of the invention are described with reference to illustrative embodiments, wherein like numerals reference like elements, and wherein:

FIG. 3 is a schematic diagram of a ligament repair arrangement in accordance with known repair techniques;

FIG. 4 shows a schematic diagram of a ligament repair in accordance with aspects of the invention;

FIG. 5 shows a schematic diagram of a ligament repair in which the repair material includes an integrally formed fixation member;

FIG. 6 shows a schematic diagram of an opening formed in a bone in one illustrative embodiment;

FIG. 7 shows a schematic diagram of a repair material being inserted in to an opening formed like that in FIG. 6;

DETAILED DESCRIPTION

Figure 1:
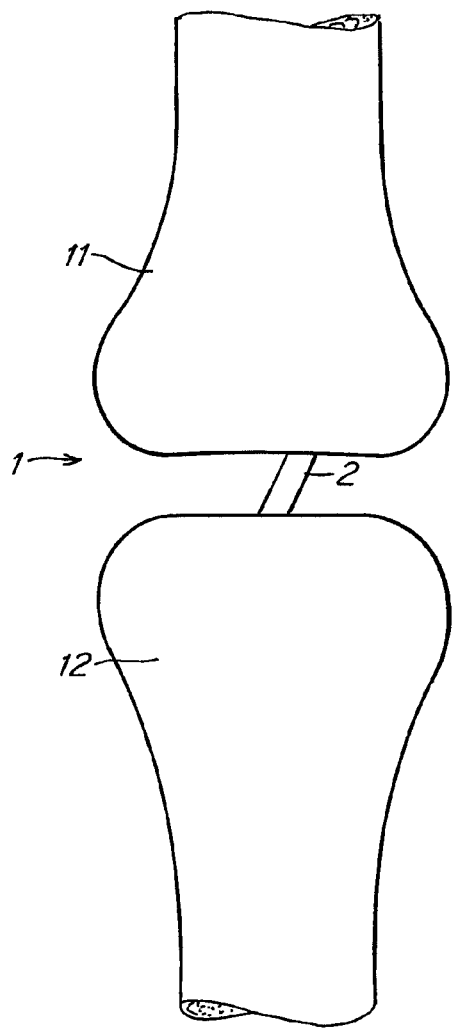
FIG. 1 is a schematic diagram of a knee and attached ligament.
Figure 2:
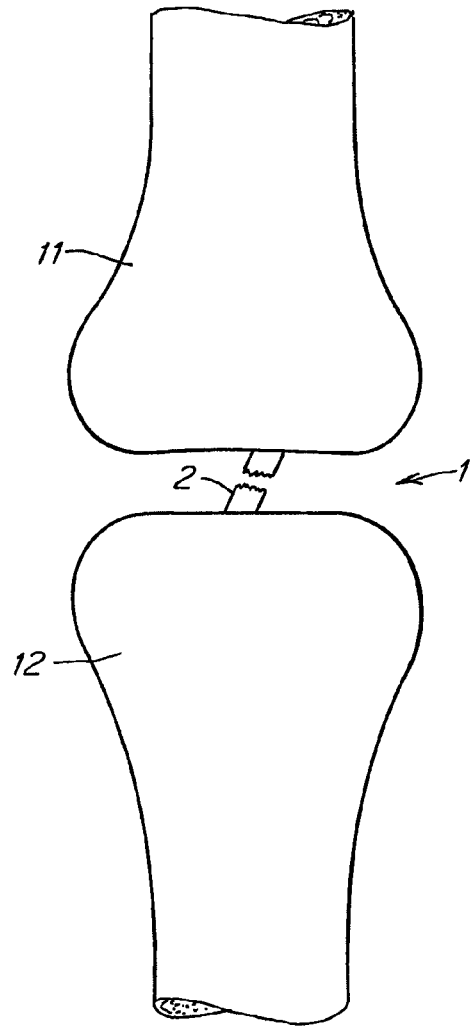
FIG. 2 is a schematic diagram of a knee with a ligament injury.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting.

Various aspects of the invention are described below with reference to specific embodiments. For example, aspects of the invention are described in the context of performing a knee ligament repair. However, it should be understood that aspects of the invention are not necessarily restricted to knee ligament repair techniques, or even to surgical techniques performed on a knee. Rather, various aspects of the invention may be used in any suitable surgical procedure. In addition, various aspects of the invention may be used alone, and/or in combination with any other aspects of the invention.

FIG. 4 shows a schematic diagram of a surgical repair in accordance with aspects of the invention. As discussed above, although aspects of the invention are described with reference to a knee ligament repair for ease of reference and understanding, aspects of the invention may be used in any surgical or other procedure, and may involve any suitable body portions, such as bone, muscle, other tissue or combinations thereof, vascular structures, digestive structures, medical implants or other devices, etc. Thus, aspects of the invention are in no way limited to the specific embodiments and examples described herein.

In this illustrative embodiment, a ligament 2, such as an anterior cruciate ligament (ACL) 2 has been damaged and is replaced by a repair material 4. The repair material 4 may be an allograft or autograft of knee ligament material, such as ligament material harvested from a patient's patella or a harvested hamstring tendon, etc. The repair material 4 may optionally be a man-made material, such as a mesh or other prosthetic device. In short, the repair material 4 may be any suitable material or combination of materials for the repair.

In accordance with one aspect of the invention, one end of the repair material 4 is secured relative to a bone via contact with an internal area of cortical bone. Thus, the repair material 4 may be robustly fixed in place without necessarily requiring an interference screw, an expanding anchor, or other similar device. In this illustrative embodiment, the repair material 4 engages with an internal contact area 5 of the tibia 12, but it should be understood that a similar engagement may be made with a contact area 5 in the femur 11. By engaging the repair material 4 with a cortical bone contact area 5, the repair material 4 can be solidly anchored relative to the bone with a minimal risk of movement of the contact area 5, e.g., in the direction of tension tending to pull the repair material 4 out of the tibia 12 and toward the femur 11. This is not necessarily the case with anchoring arrangements that engage the repair material 4 with cancellous bone, which may compress or otherwise give way when the repair material 4 is placed under tension or other stress.

The contact area 5 may be formed in the bone in any suitable way. For example, in the embodiment shown in FIG. 4, a passageway 6 may be initially formed through the tibia 12 such that the passageway 6 has an approximately constant diameter from a first opening 61 to a second opening 62 near the knee joint. This passageway 6 may be formed in any suitable way, such as those known in the art including drilling, punching or other. Thereafter, the passageway 6 may be counterbored in a direction from the first opening 61 toward the second opening 62 so that the first opening 61 has a larger diameter than the second opening 62. The counterbore may be formed by using a drill of a larger size than the passageway's initial size, a reaming tool, a punch, etc. The contact area 5 may be formed by the tool used to form the counterbore, or may be formed separately, such as by a tamping device, reamer, etc. that crushes and/or moves cancellous bone so as to expose a cortical bone area to serve as the contact area 5. The contact area 5 may have an annular shape and be arranged in a plane that is perpendicular (or otherwise generally transverse) to the longitudinal axis of the passageway 6 (or to the general direction in which tension is applied to the repair material 4). However, the contact area 5 is not limited to flat, annular arrangements, but instead may have a conical or semi-conical shape, may be rectangular, oval, triangular, etc. Also, the contact area 5 need not necessarily be flat, but may have bumps, ridges, grooves or other features.

The repair material 4 may be secured to the contact area 5 in any suitable way, such as by one or more fixation devices that are formed separately from and attached to the repair material, and/or by a component that is integrally formed with the repair material. For example, the repair material 4 may be secured to a bushing-like member or other device that has at least one portion that is larger than the size of the second opening 62. As a result, if the repair material 4 is fed through the passageway 6 from the first opening 61 and pulled through the second opening 62, the bushing-like member may engage with the contact area 5, preventing the repair material 4 from being further pulled from the second opening 62.

In another illustrative embodiment, the repair material may have an integrally formed member that engages with the contact area 5. For example, as shown in FIG. 5, an autograft ligament 4 that is harvested from a patient's patella tendon may include bone blocks on either end of the tendon. The bone blocks may be shaped or otherwise suitably arranged so that a bone block at a first end 41 of the tendon may pass through the second opening 62, allowing the tendon portion to be pulled through the second opening 62 as well. However, the bone block at the second end 42 of the tendon may be larger than the second opening 62, and thus engage with the contact area 5 to secure the tendon in place. In another embodiment, a synthetic repair material may include an integrally formed stop member or other portion that engages with the contact area 5.

In another illustrative embodiment, the opening formed in the bone for securing a repair material need not be formed as a passageway that extends from one opening through the bone to another opening. Instead, as shown in FIG. 6, the opening 6 may partially extend into the bone 12, and be arranged so that a contact area 5 is provided beneath the outer surface of the bone 12. In this embodiment, the opening 6 may be formed in any suitable way, such as by first drilling a hole into the bone, and then enlarging the size of the hole beneath the surface of the bone to form the contact area 5 in the bone's cortical region. The repair material 4 may be secured in the opening 6 in any suitable way, such as by an expanding anchor-type fixation device that is secured to the repair material 4, inserted through the opening, and then expands at least in part to engage the contact area 5. In another embodiment, the opening 6 may be formed to have an oblong or other suitable shape as shown in FIG. 7. The repair material 4 may have a complementary fixation device 7 that is inserted through the opening 6, and then rotated in the opening 6 so that the fixation device 7 engages the contact area 5 and prevents the fixation device 7 from being pulled from the opening 6. The fixation device 7 may be formed in any suitable way. For example, the fixation device 7 may be a suitably shaped bone block that is part of a harvested patella tendon, as described above. Alternately, the fixation device 7 may be a separately formed component that is secured to a ligament or other repair material 4.

Figure 8:
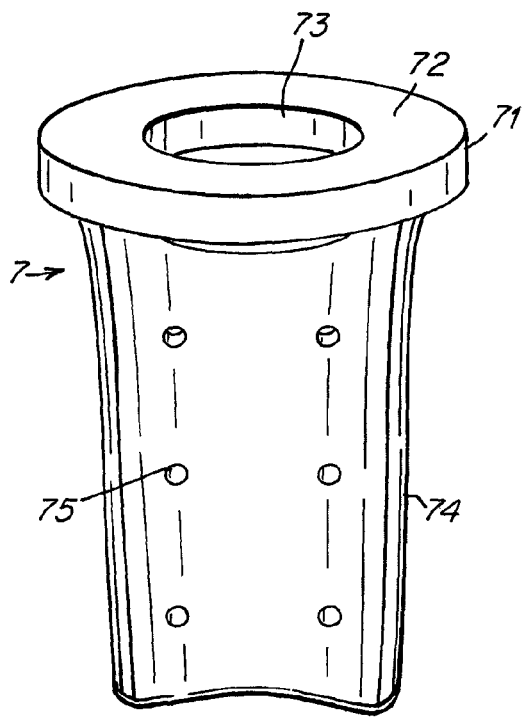
FIG. 8 shows a perspective view of a fixation device in an illustrative embodiment.

FIG. 8 shows a schematic view of a fixation device 7 in one illustrative embodiment. The fixation device 7 includes a base portion 71, which in this embodiment is an annular-shaped flange, with a contact surface 72 arranged to engage with the contact area 5 in a bone. The base portion 71 includes an aperture 73 to receive a ligament or other repair material 4. Although in this embodiment, the base portion 71 is shown to form a closed loop around the aperture 73, the base portion 71 need not do so, and may have one or more splits or gaps in the base portion 71. Also, the base portion 71 need not have an annular shape as shown, but may have an oval, rectangular, triangular, elongated or other suitable shape. Generally, the contact surface 72 will be flat, but may be arranged in other ways, such as to include serrations, bumps, grooves or other suitable features.

Figure 9:
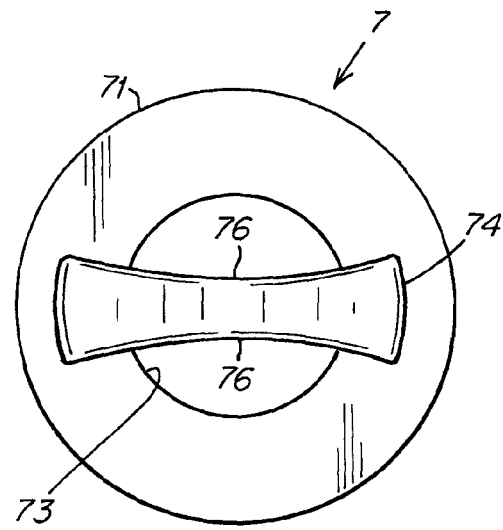
FIG. 9 shows a bottom view of the fixation device of FIG. 8.

A securing portion 74 may have an elongated shape and extend from the base portion 71 in a direction away from the contact surface 72. One or more holes 75 or other features may be provided in the securing portion 74, e.g., to receive suture for securing a repair material 4 to the securing portion 74. As can be seen in the bottom view of FIG. 9, the securing portion 74 may include opposed grooves 76 to receive the repair material 4. Also, the securing portion 74 may taper along a central region from the distal end (farthest from the base portion 71 as shown in FIG. 9) to a proximal end (nearest the base portion 71 as shown in the top view of FIG. 10). This taper may help in passing the repair material through the aperture 73 (because of the relatively small thickness of the securing portion 74 near the aperture 73) and in positioning the repair material 4 against the walls of the bone opening (the thicker portion of the securing portion 74 may urge the repair material 4 into contact with the bone at and near the distal end) to encourage ingrowth of the bone or otherwise encourage healing processes that secure the repair material 4 to the bone. Thus, in one embodiment, the securing portion 74 may have a Y-shape with two legs attached to the base portion 71 and another leg extending away from the base portion 71.

Figure 11:
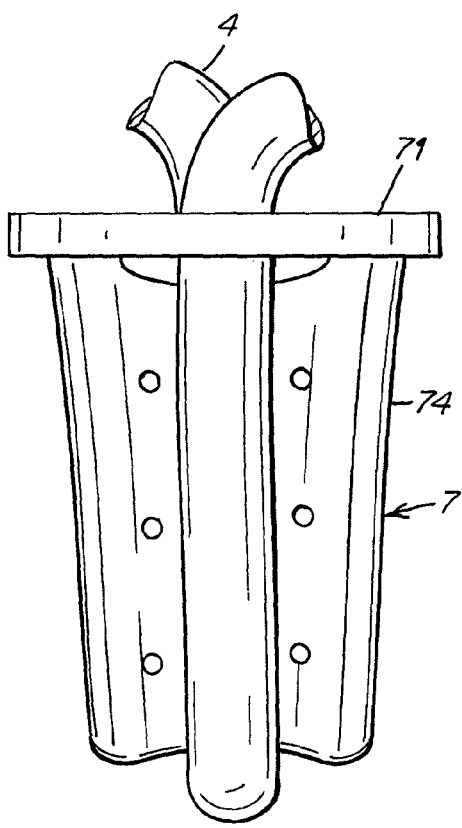
FIG. 11 shows a side view of the fixation device of FIG. 8 with a repair material attached.
Figure 10:
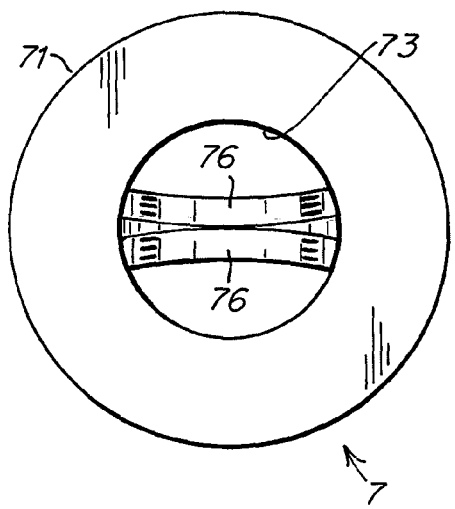
FIG. 10 shows a top view of the fixation device of FIG. 8.

FIG. 11 shows a repair material 4 (in this example a ligament graft) engaged with the fixation device 7 of FIGS. 8-10. The repair material 4 passes through the aperture 73 and extends along a first groove 76 of the securing portion 74. The repair material 4 then extends over the distal end of the securing portion 74 and down the opposed second groove 76 and through the aperture 73. (In another embodiment, two strands of repair material 4 may pass through the aperture 73 and extend along opposed grooves 76 of the securing portion 74, terminating distally of the distal end of the securing portion 74.) Suture, clips or other securing material (not shown) may engage the repair material 4 and the securing portion 74 at the holes 75 or otherwise to help keep the repair material 4 in place relative to the fixation device 7. In one illustrative embodiment, the repair material 4 may have a diameter of about 8-11 mm, with the aperture 73 having approximately the same size (e.g., 8-11 mm) and the outer diameter of the base portion 71 being about 10-15 mm. The length of the securing portion 74 may be about 10-25 mm, or more or less, as suitable for the application. The fixation device 7 may be made of any material or suitable combination of materials, including non-absorbable/biocompatible materials (such as titanium, stainless steel, other alloys, etc.), absorbable materials (such as PLA, PGA, reprocessed bone, and other materials, mixtures or composites), or combinations of materials. The fixation device 7 may also be coated with or otherwise include materials that encourage bone growth, such as an osteo-conductive or osteo-inductive material.

Although in this embodiment, the fixation device 7 is shown as formed as a unitary piece, e.g., molded of a suitable material, the fixation device 7 may be made in two or more separate parts. For example, the base portion 71 and the securing portion 74 may be made separately and assembled on a repair material. The securing portion 74 may then engage the base portion 71 by way of interference to resist pulling of the repair material 4 and the securing portion 74 through the aperture 73. For example, in an application like that shown in FIG. 7, the repair material may first threaded through the aperture 73 of a base portion 71, and then engaged with a separate securing portion 74. Thereafter, the securing portion 74 and repair material 4 may be inserted into the opening 6, followed by the base portion 71 being inserted in the opening 6. The base portion 71 may be arranged in the form of a split ring (e.g., a flat annular washer-like device with a cut or gap) such that the base portion 71 may be forced through the opening 6 (e.g., by folding or deforming the base portion 71 to reduce its size). The base portion 71 may then be oriented to engage the contact area 5 and the securing portion 74 may be seated against the base portion 71 to secure the repair material 4. In another embodiment, the base portion 71 may have an oval, rectangular, oblong or other shape such that the base portion 71 may be passed through the opening 6, and then turned or otherwise oriented so that the base portion 71 cannot be pulled through the opening 6.

In other illustrative embodiments, the securing portion 74 may include two or more portions to help secure the repair material 4, to help engage the repair material with bone in the opening, and/or to perform other functions. For example, the securing portion 74 may include a sleeve that is located over the repair material 4 after the material 4 is engaged with the securing portion 74 as shown in FIG. 11. The sleeve may help secure the repair material 4 in place, as well as help encourage bone ingrowth. In another embodiment, the securing portion 74 may be made to expand in diameter, e.g., when tension is placed on the repair material after deployment of the fixation device 7. Expansion of the securing portion 74 may help urge the repair material 4 into contact with the bone in the walls of the opening 6. Expansion may occur as a result of the design of the securing portion 74, e.g., the securing portion may be made hollow or otherwise deformable in at least a portion so that the securing portion 74 buckles outwardly with tension applied to the repair material. Alternately, insertion of an interference pin, screw or other device into the securing portion 74 may expand a portion of the securing portion 74 and force the repair material into contact with the wall of the opening. In other embodiments, the repair material 4 may be secured to the securing portion 74 using interference screws or pins, or other devices.

Figure 12:
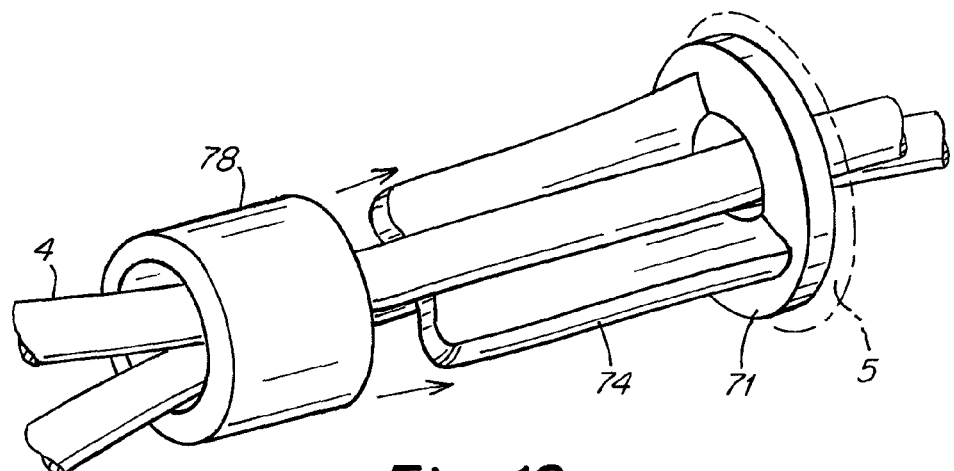
FIG. 12 shows a perspective view of a fixation device in another illustrative embodiment.
Figure 13:
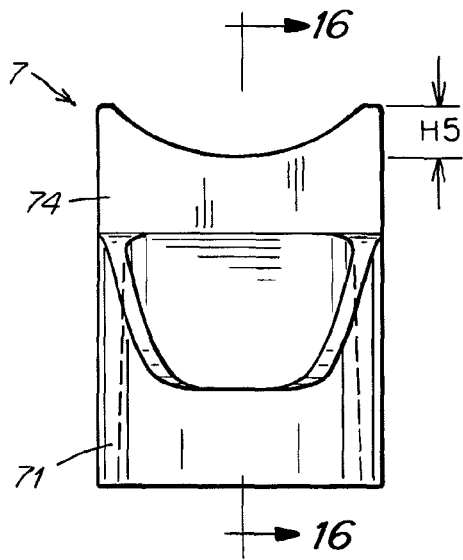
FIG. 13 shows a front view of a fixation device in yet an illustrative embodiment.
Figure 14:
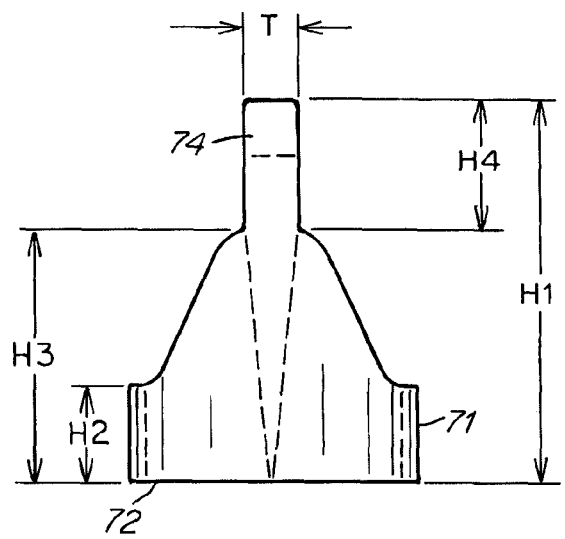
FIG. 14 shows a side view of the fixation device of FIG. 13.
Figure 15:
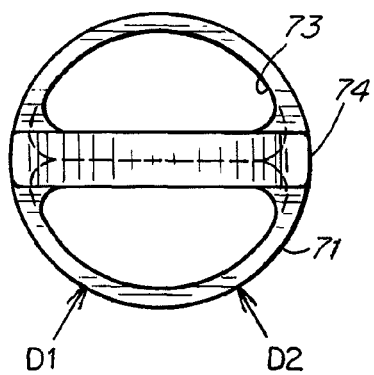
FIG. 15 shows a top view of the fixation device of FIG. 13.
Figure 16:
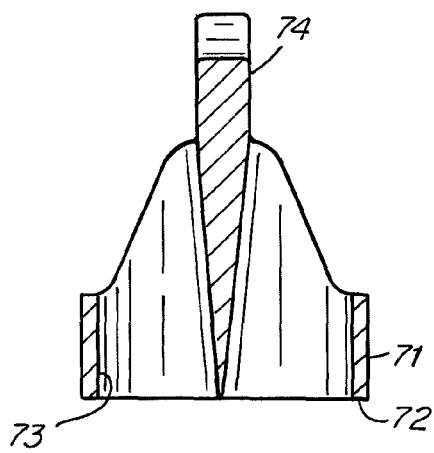
FIG. 16 shows a cross sectional view of the fixation device along the line 16-16 in FIG. 13.

In the embodiments above, the repair material 4 is first secured at the contact area 5, e.g., of the tibia 12, and then an opposite, second end of the repair material 4 is secured to another bone, e.g., the femur 11. However, it should be understood that aspects of the invention are not so limited. Instead, the repair material 4 may be first secured (e.g., to a tibia 12) using the techniques described above or any other suitable method, and then secured to a cortical contact area 5 (e.g., in a femur 11). Although securing of the repair material to the contact area 5 may be performed using the devices described above, FIG. 12 shows another illustrative embodiment of a fixation device 7 that allows for tensioning of the repair material, and subsequent fixation to the device 7. The fixation device 7 may be constructed largely as described above with a base portion 71 and securing portion 74. With the base portion 71 seated against the contact area 5, the repair material 4 may be pulled through the aperture 73 (with the fixation device 7 held in contact with the contact area 5 of the bone) until suitable tension is applied. Thereafter, a sleeve 78 may be engaged over the securing portion 74 and the repair material 4 to secure the repair material 4 to the securing portion 74. This securing operation may be performed in other ways as well. For example, the securing portion 74 may be formed as a sleeve or cylindrical member with the repair material 4 passing through the interior of the sleeve. To secure the repair material 4 in place, an interference pin, screw or other member may be inserted into the sleeve, forcing the repair material into contact with the securing portion 74. The securing portion 74 may have slots or other openings to allow tissue ingrowth.

FIGS. 13-16 show front, side, top and sectional views of a fixation device 7 in another illustrative embodiment. This embodiment is similar to that shown in FIGS. 8-11, but has a cylindrically shaped part that includes an annular base portion 71 with an annular contact surface 72. The securing portion 74 has a wedge-like shape and extends approximately diametrically across the aperture 73 defined by the base portion 71. Although in this embodiment the securing portion 74 does not include grooves 76 or holes 75 like that in the FIGS. 8-11 embodiment, such features may be included if desired. This embodiment has the following dimensions, although it should be appreciated that the dimensions may be varied as desired: an overall height H1 of about 15 mm, a base height H2 of about 4 mm, an intermediate height H3 of about 10 mm, an upper height H4 of about 5 mm, an upper groove depth H5 of about 2 mm, a securing portion upper thickness T of about 2 mm, an overall diameter D1 of about 11 mm, and an inner diameter D2 of about 10 mm. Although not shown, in this embodiment the base portion 71 may include a separate washer or other device (e.g., shaped like the base portion 71 shown in FIG. 8 and that is separate from the cylindrical part) that contacts the base portion 71 at the contact surface 72 and engages the contact area 5 of the bone. The washer may be split (e.g., like a conventional lock washer used with bolts or screws) to allow the washer to be reduced in size and inserted into an opening 6. Thereafter, the washer may expand to its original shape to engage with the contact area 5 and provide an engagement surface for the base portion 71.

It should be understood that aspects of the invention include repair techniques in which a repair material is secured to a cortical contact area 5 of a bone at one or more ends of the repair material. Moreover, if one portion of a repair material 4 is secured to a cortical contact area 5, other portions of the repair material 4 may be secured to the same or different bone using any suitable technique or device, as are known in the art, such as interference screws, etc. In addition, fixating a repair material via a cortical contact area may be supplemented by additional securing techniques, such as conventional interference screw fixation.

Although various embodiments have been described above in the context of a knee ligament repair, aspects of the invention may be used in other applications, such as rotator cuff repair or other tendon repair, hernia mesh fixation, and others.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:
1. A surgical fixation device, comprising:
   a base portion including an aperture constructed and arranged to receive a graft configured to replace a ligament or tendon, the base portion having a contact surface at a first side and being constructed and arranged to contact a bone at the contact surface and secure the graft relative to the bone surface; and a securing portion constructed and arranged to secure the graft to the base portion, the securing portion being arranged to engage with the base portion on a second side of the base portion opposite the contact surface and extending from the second side in a direction away from the contact surface of the base portion, the securing portion having a part that extends across the aperture without occluding the aperture when the securing portion is engaged with the second side of the base portion;

wherein the base portion and the securing portion are arranged to be deployed entirely within a bone opening and to anchor the graft relative to bone in the bone opening to resist tension experienced by a replacement ligament or tendon where the tension is applied on the graft, while the graft is secured to the securing portion and passes through the aperture, in a direction from the securing portion toward the contact surface, wherein the base portion and securing portion are arranged to receive the graft such that a portion of the graft passes through the aperture, extends along a first side of the securing portion toward a distal end of the securing portion, passes over the distal end of the securing portion, and then extends along a second side of the securing portion away from the distal end and back through the aperture, and wherein the securing portion is configured to expose the graft to bone in the bone opening along at least a portion of a length of the securing portion when the graft is anchored by the surgical fixation device relative to bone in the bone opening.

2. The device of claim 1, wherein the securing portion tapers so as to be thinner in a proximal region near the aperture and so as to be thicker in a distal region positioned away from the aperture.

3. The device of claim 1, wherein the securing portion has an elongated shape that extends away from the base portion.

4. The device of claim 1, wherein the base portion includes a circular flange with an annular contact surface.

5. The device of claim 1, wherein the base portion includes a circular aperture.

6. The device of claim 1, wherein the securing portion includes opposed grooves to receive the graft.

7. The device of claim 1, wherein the securing portion includes one or more openings adapted to receive a suture to secure the graft to the securing portion.

8. The device of claim 1, wherein the base portion includes a cylindrical portion that defines the aperture, and where the securing portion has a wedge-like shape that is fixed to the cylindrical portion and extends into and across the aperture.

9. The device of claim 1, wherein the aperture is defined by a closed loop of the base portion, and the securing portion extends across the aperture.

10. The device of claim 9, wherein the securing portion tapers along its length so as to be thinner in a proximal region near the aperture and so as to be thicker in a distal region positioned away from the aperture.

11. The device of claim 1, wherein the base and securing portions are made of an absorbable material.

12. The device of claim 1, wherein the base and securing portion are adapted to be used in a knee ligament repair procedure.

13. The device of claim 1, wherein the base and securing portion are adapted to be used in a knee ligament repair procedure using subcortical bone fixation of the graft.

14. The device of claim 1, wherein the base portion includes a washer element having an annular shape, that defines the contact surface, and that is split to allow a reduction in size of the washer element.

15. A surgical fixation device, comprising:
an annular portion having a bone contact surface on a first side and an opening adapted to receive a graft configured to replace a ligament or tendon; and
a securing portion attached to a second side of the annular portion opposite the first side and having a portion that extends across the opening of the annular portion without occluding the opening when the securing portion and annular portion anchor the graft relative to bone, the securing portion having an elongated member extending in a direction away from the contact surface and being adapted to secure a graft passing through the opening of the annular portion;
wherein the annular portion and the securing portion are arranged to be deployed entirely within a bone opening and to anchor the graft relative to bone in the bone opening to resist tension experienced by a replacement ligament or tendon where the tension is applied on the graft, while the graft is secured to the securing portion and passes through the opening, in a direction from the securing portion toward the contact surface, wherein the annular portion and securing portion are arranged to receive the graft such that a portion of the graft passes through the opening, extends along a first side of the securing portion toward a distal end of the securing portion, passes over the distal end of the securing portion, and then extends along a second side of the securing portion away from the distal end and back through the opening, and wherein the securing portion is configured to expose the graft to bone in the bone opening along at least a portion of a length of the securing portion when the graft is anchored by the surgical fixation device relative to bone in the bone opening.

16. The device of claim 15, wherein a distal end of the elongated member located away from the annular portion has a groove to receive the graft.

17. The device of claim 15, wherein the elongated member of the securing portion includes opposed grooves to receive the graft.

18. The device of claim 15, wherein the securing portion includes one or more openings adapted to receive a suture to secure the graft to the securing portion.

19. The device of claim 15, comprising a cylindrical portion that includes the annular portion and defines the opening, and wherein the elongated member has a wedge-like shape that is fixed to the cylindrical portion and extends into and across the opening.

20. The device of claim 15, wherein the securing portion extends across the opening and is attached to diametrically opposed portions of the annular portion.

21. The device of claim 20, wherein the securing portion tapers so as to be thinner in a region near the opening and so as to be thicker in a region positioned away from the opening.

22. The device of claim 15, wherein the base and securing portions are made of an absorbable material.

23. The device of claim 15, wherein the annular and securing portion are adapted to be used in a knee ligament repair procedure.

24. The device of claim 15, wherein the base and securing portion are adapted to be used in a knee ligament repair procedure using subcortical bone fixation of the graft.

25. The device of claim 15, wherein the annular portion includes a washer element having a flange-like shape and that is split to allow a reduction in size of the washer element.

26. A surgical fixation device, comprising:
a base portion including an aperture constructed and arranged to receive a graft configured to replace a ligament or tendon, the aperture being defined by a closed loop of the base portion, the base portion having a contact surface and being constructed and arranged to contact a bone at the contact surface and secure the graft relative to the bone surface; and a securing portion constructed and arranged to secure the graft to the base portion, the securing portion being attached to the base portion on a side of the base portion opposite the contact surface and extending away from the base portion, the securing portion having a part that extends across the aperture without occluding the aperture when the securing portion and base portion anchor the graft relative to bone;

wherein the base portion and the securing portion are arranged to be deployed entirely within a bone opening and to anchor the graft relative to bone in the bone opening to resist tension experienced by a replacement ligament or tendon, where the tension is applied on the graft secured to the securing portion and passing through the aperture, in a direction from the securing portion toward the contact surface, wherein the base portion and securing portion are arranged to receive the graft such that a portion of the graft passes through the aperture, extends along a first side of the securing portion toward a distal end of the securing portion, passes over the distal end of the securing portion, and then extends along a second side of the securing portion away from the distal end and back through the aperture, and wherein the securing portion is stationary relative to the base portion and is configured to remain stationary relative to the base portion throughout the deployment of the base portion and the securing portion into the bone opening and the anchoring of the graft.

27. A repair apparatus comprising:
a surgical fixation device according to claim 1, and
a graft configured to replace a ligament or tendon, the graft having a portion that extends through the aperture of the base portion and is secured to the surgical fixation device at the securing portion.

28. A repair apparatus comprising:
a surgical fixation device according to claim 15, and
a graft configured to replace a ligament or tendon, the graft having a portion that extends through the opening of the base portion and is secured to the surgical fixation device at the securing portion.

29. A repair apparatus comprising:
a surgical fixation device according to claim 26, and
a graft configured to replace a ligament or tendon, the graft having a portion that extends through the aperture of the base portion and is secured to the surgical fixation device at the securing portion.

30. The device of claim 1, wherein the aperture of the base portion includes a pair of openings.

31. The device of claim 30, wherein the securing portion has a portion that extends into and across the aperture to define the pair of openings.

32. The device of claim 1, wherein the part of the securing portion that extends across the aperture is located distal of the aperture.

33. The device of claim 15, wherein the opening of the annular portion includes two portions.

34. The device of claim 33, wherein the securing portion extends into and across the opening to define the two portions of the opening.

35. The device of claim 15, wherein the part of the securing portion that extends across the opening is located distal of the opening.

36. The device of claim 26, wherein the aperture of the base portion includes a pair of openings.

37. The device of claim 36, wherein the securing portion has a portion that extends into and across the aperture to define the pair of openings.

38. The device of claim 26, wherein the part of the securing portion that extends across the aperture is located distal of the aperture.

39. The device of claim 26, comprising a cylindrical portion that includes the base portion and defines the aperture, and wherein the securing portion includes a wedge-like shape that is fixed to the cylindrical portion and extends into and across the aperture.

40. The device of claim 26, wherein the securing portion extends across the aperture and is attached to diametrically opposed portions of the base portion.

41. The device of claim 26, wherein the base and securing portion are adapted to be used in a knee ligament repair procedure using subcortical bone fixation of the graft.

* * * * *